United States Patent [19]
Landgrebe et al.

[11] Patent Number: 5,840,011
[45] Date of Patent: Nov. 24, 1998

[54] IMPLANT FOR SUSPENSION OF THE URINARY BLADDER IN CASES OF INCONTINENCE OF URINE IN WOMEN

[75] Inventors: Susanne Landgrebe, Norderstedt; Lothar Schilder, Hamburg, both of Germany

[73] Assignee: Ethicon, Inc., Somerville, N.J.

[21] Appl. No.: 756,082

[22] Filed: Nov. 25, 1996

[30] Foreign Application Priority Data

Nov. 17, 1995 [DE] Germany ............... 195 44 162.1

[51] Int. Cl.⁶ .............................................. A61F 2/02
[52] U.S. Cl. ...................................... 600/30; 600/29
[58] Field of Search ............... 623/11, 12; 600/29–31; 128/DIG. 25, 885, 887, 834, 836

[56] References Cited

U.S. PATENT DOCUMENTS

| | | | |
|---|---|---|---|
| 3,863,622 | 2/1975 | Buuck | 600/31 |
| 4,920,986 | 5/1990 | Biswas | 128/885 |
| 5,393,594 | 2/1995 | Koyfman et al. | 442/414 |
| 5,464,416 | 11/1995 | Steckel | 606/158 |
| 5,562,724 | 10/1996 | Vorwerk et al. | 623/1 |

*Primary Examiner*—John P. Lacyk
*Assistant Examiner*—Rosilund Kearney
*Attorney, Agent, or Firm*—Emil Richard Skula

[57] ABSTRACT

An implant for suspension of the urinary bladder in bases of incontinence of urine in women has a flat, flexible basic structure. Two first projections (5, 6) and two second projections (7, 8) start from a triangle-like to elongated oval basis (1). The two first projections (5, 6) run on opposite sides of the longitudinal axis (L—L) of the base (1), and the two second projections (7, 8) likewise run on opposite sides of the longitudinal axis (L—L) of the base (1), but generally in the opposite direction to the two first projections (5, 6).

7 Claims, 1 Drawing Sheet

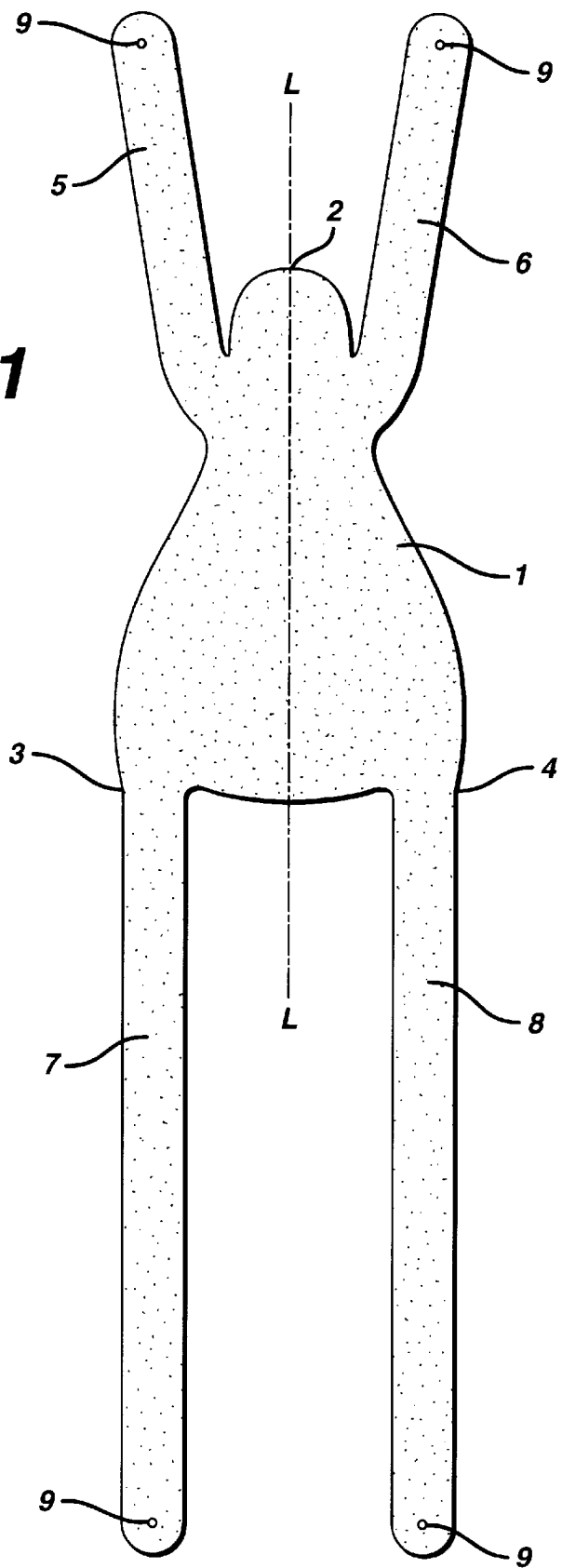

IMPLANT FOR SUSPENSION OF THE URINARY BLADDER IN CASES OF INCONTINENCE OF URINE IN WOMEN

TECHNICAL FIELD

The invention relates to an implant for suspension of the urinary bladder in cases of incontinence of urine in women.

BACKGROUND OF THE INVENTION

Treatment of incontinence of urine in women is distinguished by a large number of different treatment concepts. While milder forms of stress incontinence can still be treated successfully by training of the pelvic floor and pharmacological treatment, only surgical treatment remains for severe forms of incontinence of urine. The aims of surgical treatment are to achieve anatomically adequate and permanent displacement of the neck of the bladder cranio-ventrally in the abdominal pressure region, and in the event of descensus genitalis and prolapse to take reconstructive measures to render the insufficient suspension and support apparatus capable to carrying the load again.

About 200 operating methods, modifications and modified modifications demonstrate the disagreement in the therapeutic procedure. In view of the multifactorial development of stress incontinence, the surgeon as a rule chooses the method which most closely meets the requirements existing in the individual case. Transvaginal and suprapubic accesses are combined, as are gathering of tissue, fixations and suspending bridles of fascial ribbon, lyodura or alloplastic material. The individually different constellations of findings do not allow a general preference to be given to a particular operating method. Rather, is a matter of carefully choosing, considering and deciding from the entire range of therapeutic possibilities available.

DISCLOSURE OF INVENTION

The object of the invention is to provide an implant for reliable treatment of incontinence of urine in women, especially in cases of extreme weakness of the pelvic floor with prolapsing anatomical displacement of the organs of the lesser pelvis, and in patients following several unsuccessful previous operations using the usual techniques.

This object is achieved by an implant for suspension of the urinary bladder in cases of incontinence of urine in women, having the features of claim 1. Advantageous embodiments result from the sub-claims.

After the implant according to the invention has been inserted in a surgical operation, as described below, the urinary bladder lies with a wide surface area on the implant, which means that an absolutely stable bilateral fixation of the urinary bladder is achieved both in the bladder neck region and in the region of the apex of the bladder. By hanging at four points by means of the two first projections and the two second projections starting from the base of the basic structure of the implant, the urinary bladder is supported elastically as on a hammock as a result of the implant, regardless of the condition of the pelvic floor. Renewed prolapse or descensus even under load can thus reliably be avoided. With the implant according to the invention, not only the bladder outlet but the entire urinary bladder is incorporated in a broad stable support which supports the entire base of the bladder. This results in no increase in discharge resistance, but exclusively stress-proof relieving of the sphincter vesicae externus. There is no risk of obstruction if the implant is incorporated correctly.

In a preferred embodiment, the basis structure of the implant has several layers. In this, a net of polypropylene, which is not absorbable, can be provided with a porous coating of an absorbable composite material of polyglactin 910 (a copolymer of glycolide and lactide in a ration of 9:1) and polydioxanone on both sides.

In the course of breakdown of the absorbable contents of the implant in the body, replacement of these contents by connective tissue with construction through the net, which remains permanently, takes place. The net is therefore secured from dislocation and the surrounding tissue is protected from mechanical irritation or erosion. A stable, permanent suspension os the bladder results.

The invention is described in more detail below with the aid of an embodiment example.

BRIER DESCRIPTION OF THE DRAWINGS

The drawing shows in

FIG. 1 shows a plan view of an embodiment of an implant according to the invention. The implant comprise a flat, flexible basic structure.

DESCRIPTION OF PREFERRED EMBODIMENTS

A base 1 is triangle-like to elongated oval in shape and has a longitudinal axis L—L. In the embodiment example, the base 1 rather resembles a triable with the corners 2, 3 and 4, the corner 2 (through which the longitudinal axis L—L of the base 1 runs) being rounded. The area of the base is about 30–50 cm$^2$.

From the base 1, close to the corner 2 but at a distance from this, a first projection 5 which is bridle-like in construction starts. The first projection 5 runs on the left-hand side of the longitudinal axis L—L at a sharp angle with respect to the longitudinal axis L—L, which is less than 20° in the embodiment example. Another first projection 6 which has the same form as the first projection 5 is arranged in morrow symmetry to the longitudinal axis L—L.

From the corner 3 of the base 1, a second projection 7 which runs on the left-hand side of the longitudinal axis L—L and essentially parallel to this starts. The second projection 7 is thus generally directed in the opposite direction to the first projection 5, i.e. while the first projection 5 in FIG. 1 extends (at an angle) upward, the second projection 7 runs downwards. Like the first projection 5, the second projection 7 could also form an angle to the longitudinal axis L—L of the base 1 which differs from 0°. From the corner 4 of the base 1, another second projection 8 which runs in mirror image to the second projection 7 in respect of the longitudinal axis L—L starts. The two second projections 7 and 8 have the same dimension and are longer than the two first projections 5 and 6.

Between the two first projections 5 and 6, in the region of the corner 2, the base forms a semicircular or oval extension about 2–3 cm$^2$ in area. The purpose of this extension is suspension of the bladder neck and of the proximal urethra, so that after the implant has been inserted, complete support of the base of the bladder, bladder neck and proximal urethra is achieved overall.

Holes 9 which can be of assistance during insertion and fixing (suturing in place) of the implant can be provided close to the ends of the first projections 5 and 6 and of the second projections 7 and 8.

In the embodiment example, the implant has three layers. The middle layer comprises a non-absorbable, flexible net of 0.7 mm thickness made from monofilament polypropylene threads. This material does not lose its physical properties in the body in the long-term, and is insensitive to variations in pH. It is elastic and unidirectionally extendable, to allow changes in shape, such as exist, for example, during pressure on the abdomen, due to the filling level of the bladder or during micturition.

A porous coating of an absorbable composite material comprising polyglactin 910 and polydioxanone is applied to both sides of the polypropylene net. In the embodiment example, these outer layers are absorbed without residue within about 120 days after implantation.

The basic idea of this material combination is to combine the connective tissue-conductive properties of the layers of the composite material, which are preferably constructed as nonwoven layers (fleece), with the permanent stability of the polypropylene net. Findings from animals experiments show that a large quantity of fibrohistiocytic tissue is constructed through the nonwoven layer on the surface within the first three weeks. In particular, filaments of polyglactin 910 serve as conductors for the formation of aligned collagenic connective tissue fibers which, in contrast to scar tissue, show no tendency to shrink at all. As absorption of the outer layers progresses, loose collagenic connective tissue is constructed through the net of polypropylene and surrounds it. These healing-in processes secure the implant against dislocation and protect the surrounding tissue from mechanical irritation or erosion, with firm and permanent suspension of the urinary bladder. The good tissue compatibility of the materials used is confirmed by wide clinical use.

The bursting pressures of the implant measured in vitro are far above the forces which occur physiologically under load in humans. The implant is extendable unidirectionally by about one third of its starting length.

The implant shown in FIG. 1 has a base 1 of triangle-like shape. Deviations from this are possible. As already mentioned, the first projections 5 and 6 also do not have to un in exactly the opposite direction to the second projections 7 and 8, respectively. The precise shape of the implant can be adapted to suit the anatomical circumstances of the patient.

The build-up of the layers described for the implant and the choice of material also serve only as an example. Other tissue-compatible materials can similarly be used.

One possibility of how the implant according to the invention can be inserted in a surgical operation is described in the following example.

EXAMPLE

The spatium retropubicum is exposed by a Pfannenstiel's incision. After the apex of the bladder has been loosened from the peritoneum down to the vagina, the bladder is removed from the roof of the vagina proximally approximately a good two-finger-widths up to the bladder neck and there only approximately one-finger-width. The vessels running laterally and the ureter are to be protected carefully. This preparative procedure can be facilitated by preoperative injection under the vagina with saline solution alone or by addition of suprarenin 1:200,000. It is advisable to tampon the vagina. With an indwelling catheter, preparation is effected with an Overholt and scissors between the rear wall of the bladder and vagina distally and laterally, so that the Overholt tip can be seen on both sides paraurethrally in the spatium retropubicum.

From retrosymphyseally to both sides of the urethra/bladder neck angle, in each case a strong guide thread is drawn with the Overholt between the bladder and vagina. On these guide threads the two second projections 7, 8 or the front (proximal) bridles of the implant can be drawn retrosymphyseally between the vagina and bladder and positioned exactly, The wide base 1 of the implant comes to rest between the bladder and vagina. It should be ensure that the position of the alloplastic implant extends sufficiently far below the bladder neck in order to eliminate an existing insufficiency of the bladder neck or so that such an insufficiency cannot develop. The two first projections 5, 6 or rear (distal) retropubic bridles are passed by the urethra on both sides and fixed to the ligamentum pubicum superior behind the two pubic rami.

The rear wall of the bladder from the bladder neck to the apex of the bladder rests with a large surface area on the implant. When the implant is introduced, it is to be ensured that the often very thin wall of the bladder is not pushed towards the urethra, but is tightened abdominally. If the bladder tissue wrinkles in the region of the bladder neck, prolapse of this excess portion of the wall of the bladder may later result here.

Nevertheless, to avoid dislocation a sufficient number of tine monofilament fixation sutures (e.g. with thread thicknesses 4/0) is advisable. It is appropriate to pin the vagina to the implant on both sides with single-know sutures and thus also to incorporate the vagina into the suspension.

Before fixing the first projections 5, 6, the urinary bladder is filled with about 300 ml sale solution, to ensure that sufficient space remains for the urinary bladder to expand and to maintain an adequate bladder capacity. The two second projections 7, 8 of the implant are pulled right and left through the musculus rectus and apposed crosswise over this.

Pulling too tightly on the second projections 7, 8 carries the risk of severely limiting the retropubic space and therefore the possibility of expansion of the urinary bladder.

To avoid infection, opening of the bladder or suprapubic draining of urine should be refrained from as far as possible.

The use of the implant according to the present invention is not to be interpreted as a universal method, but is, in particular, a reliable method in extreme situations of a descensus vesicae with generalized weakness and rarification of the tissue texture in the pelvic floor. Suspension of the urinary bladder with the implant is particularly suitable in the event of pronounced recurrences, including after several previous operations. In addition to rapid postoperative mobilization, rapid occupational integration is also ensured if the floor of the pelvis is exposed to high stress due to heavy lifting. In extremely obese patients with vertical and rotatory descensus, it would be conceivable to use the implant according to the invention as a primary intervention. The essential advantage lies in the wide-area, absolutely stable, bilateral fixation of the urinary bladder both in the bladder neck region and in the region of the apex of the bladder. The urinary bladder is supported elastically as on a hammock as a result of the implant, regardless of the condition of the pelvic floor. Renewed prolapse or descensus can reliably be avoided even under load. Since with the implant not only the bladder outlet but the entire urinary bladder is incorporated in a broad fixed support which supports the entire base of the bladder, by suspension of the implant is is not an increase in the discharge resistance which is aimed for but exclusively stress-proof relieving of the sphincter vesicae externus. There is no risk of obstruction if the implant is introduced correctly.

We claim:

1. An implant for suspension of the urinary bladder useful in treating urinary incontinence, comprising a flat, flexible base structure having a top, a bottom and opposed sides; two elongated first projections extending from the top of and in the same plane as the base structure (5, 6); and two second projections (7, 8) extending from the bottom of the base structure, the two first projections (5, 6), running on opposite sides of a longitudinal axis (L—L) of the base (1) and the two second projections (7, 8) running on opposite sides of the longitudinal axis (L—L) of the base (1), said two first projections separated by a space and said two second projections separated by a space;

wherein the base structure is constructed symmetrically to the longitudinal axis (L—L) of the base (1);

wherein the two first projections (5, 6) are shorter than the two second projections (7, 8), and wherein the base (1) is substantially triangularly shaped, wherein said top which is arcuate, said top having opposed sides and the two first projections (5, 6) extend from the base (1) on opposed sides of the top through which the longitudinal axis (L—L) of the base (1) runs, but at a distance therefrom, wherein there is a continuous space between the sides of each first projection and the sides of the arcuate top such that the arcuate support the bladder neck and the proximal urethra; and, wherein the two first projections (5, 6) extend at an acute angle, which is less that 20°, with respect to the longitudinal axis (L—L) of the base (1), and in that the two second projections (7, 8), extend from the bottom of the base (1) such that they are essentially parallel to the longitudinal axis (L—L) of the base (1).

2. The implant of claim 1, wherein said base structure comprises a non-absorbable material.

3. The implant of to claim 2, wherein said non-absorbable material is polypropylene.

4. The implant of claim 1, wherein said base structure comprises an absorbable material.

5. The implant of to claim 4, wherein said absorbable material is a mixture of polyglactin 910 and polydioxanone.

6. The implant of claim 1, wherein said base structure has several layers.

7. The implant of to claim 6, wherein said base structure is built up in three layers, a net of polypropylene being provided with a porous coating of a composite material of polyglactin 910 and polydioxanone on both sides.

\* \* \* \* \*

UNITED STATES PATENT AND TRADEMARK OFFICE
CERTIFICATE OF CORRECTION

PATENT NO. : 5,840,011
DATED : November 24, 1998
INVENTOR(S) : Susanne Landgrebe, Lothar Schilder It is certified that error appears in the above-indentified patent and that said Letters Patent is hereby corrected as shown below:

Abstract: First line - "bases" should be "cases"

Signed and Sealed this

Twentieth Day of April, 1999

Attest:

Q. TODD DICKINSON

Attesting Officer     Acting Commissioner of Patents and Trademarks